(12) United States Patent
Tidwell et al.

(10) Patent No.: US 8,556,922 B2
(45) Date of Patent: Oct. 15, 2013

(54) MOTOR ASSEMBLY FOR A POWERED SURGICAL INSTRUMENT

(75) Inventors: Durrell Tidwell, Burleson, TX (US);
Jonathan Morris, Santa Rosa, CA (US);
Gabriel A. Johnston, Trophy Club, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 383 days.

(21) Appl. No.: 11/680,488

(22) Filed: Feb. 28, 2007

(65) Prior Publication Data

US 2008/0208229 A1 Aug. 28, 2008

(51) Int. Cl.
| | |
|---|---|
| A61B 17/32 | (2006.01) |
| F03C 2/00 | (2006.01) |
| F03C 4/00 | (2006.01) |
| F01C 20/00 | (2006.01) |
| F01C 21/00 | (2006.01) |
| F04C 2/00 | (2006.01) |
| F04C 14/00 | (2006.01) |
| F04C 28/00 | (2006.01) |
| F04C 15/00 | (2006.01) |
| F04C 29/00 | (2006.01) |

(52) U.S. Cl.
USPC ............. 606/167; 418/270; 418/159; 418/15

(58) Field of Classification Search
USPC ............. 606/167, 180, 159, 80, 170; 604/22;
433/29, 114, 115, 131, 132, 103;
418/15, 159, 82, 70, 270, 72, 112, 125,
418/183, 206.6, 206.7; 415/215.1, 216.1,
415/52.1; 310/50; 290/54; 451/295;
173/104, 106, 216–218; 227/176.1,
227/175.1
See application file for complete search history.

(56) References Cited

U.S. PATENT DOCUMENTS

| | | |
|---|---|---|
| 1,041,040 A | 10/1912 | Darlington |
| 3,129,642 A | 4/1964 | Sorensen et al. |
| 3,324,553 A | 6/1967 | Borden |

(Continued)

FOREIGN PATENT DOCUMENTS

| | | |
|---|---|---|
| EP | 1260190 | 11/2002 |
| RU | 1474904 | 8/1994 |
| SU | 1718849 | 3/1992 |
| SU | 1734720 | 5/1992 |

OTHER PUBLICATIONS

European Patent Office, International Search Report dated Jun. 26, 2008, Application No. PCT/US20008/053441, 2 page.

Primary Examiner — Kathleen Holwerda
Assistant Examiner — Jocelin Tanner
(74) Attorney, Agent, or Firm — Harness, Dickey

(57) ABSTRACT

A surgical instrument is provided for cutting bone and other tissue. The surgical instrument is powered by a pressurized fluid and includes a rotatable shaft connected to a dissection tool. The instrument includes a housing member comprising a one-piece base. A rotor housing chamber is defined by the base, and the rotatable shaft is located in the rotor housing chamber. A first bearing housing is defined by the base, located adjacent the rotor housing chamber, and houses a first bearing that engages the rotatable shaft. A second bearing housing is defined by the base, located on an opposite side of the rotor housing chamber from the first bearing housing, and houses a second bearing that engages the rotatable shaft. A passage is defined by the base and operable to direct a pressurized fluid through the base to the rotor housing chamber in order to rotate the rotatable shaft.

20 Claims, 6 Drawing Sheets

(56) References Cited

U.S. PATENT DOCUMENTS

| | | |
|---|---|---|
| 3,709,630 A | 1/1973 | Pohl et al. |
| 3,734,652 A * | 5/1973 | Barnett ............... 418/70 |
| 3,827,834 A | 8/1974 | Kakimoto |
| 4,631,052 A | 12/1986 | Kensey |
| 4,850,957 A | 7/1989 | Summers |
| 5,017,109 A * | 5/1991 | Albert et al. ............... 418/152 |
| 5,069,620 A | 12/1991 | Matsutani et al. |
| 5,074,750 A | 12/1991 | Kakimoto |
| 5,425,638 A | 6/1995 | Abbott |
| 5,496,173 A | 3/1996 | Wohlgemuth |
| 5,525,097 A | 6/1996 | Kakimoto |
| 5,782,836 A | 7/1998 | Umber et al. |
| 6,059,049 A * | 5/2000 | Lin ............... 173/93.5 |
| 6,273,718 B1 | 8/2001 | Schwenoha |
| 6,511,201 B1 * | 1/2003 | Elrod ............... 362/119 |
| 6,621,051 B2 * | 9/2003 | Simond ............... 219/136 |
| 7,621,730 B2 * | 11/2009 | Del Rio et al. ............... 418/270 |
| 2002/0151902 A1 * | 10/2002 | Riedel et al. ............... 606/80 |
| 2002/0165549 A1 | 11/2002 | Owusu-Akyaw et al. |
| 2005/0112526 A1 * | 5/2005 | Kuo et al. ............... 433/132 |
| 2006/0089623 A1 * | 4/2006 | Tidwell et al. ............... 606/1 |
| 2008/0093096 A1 * | 4/2008 | Chen ............... 173/221 |
| 2008/0122302 A1 * | 5/2008 | Leininger ............... 310/50 |

* cited by examiner

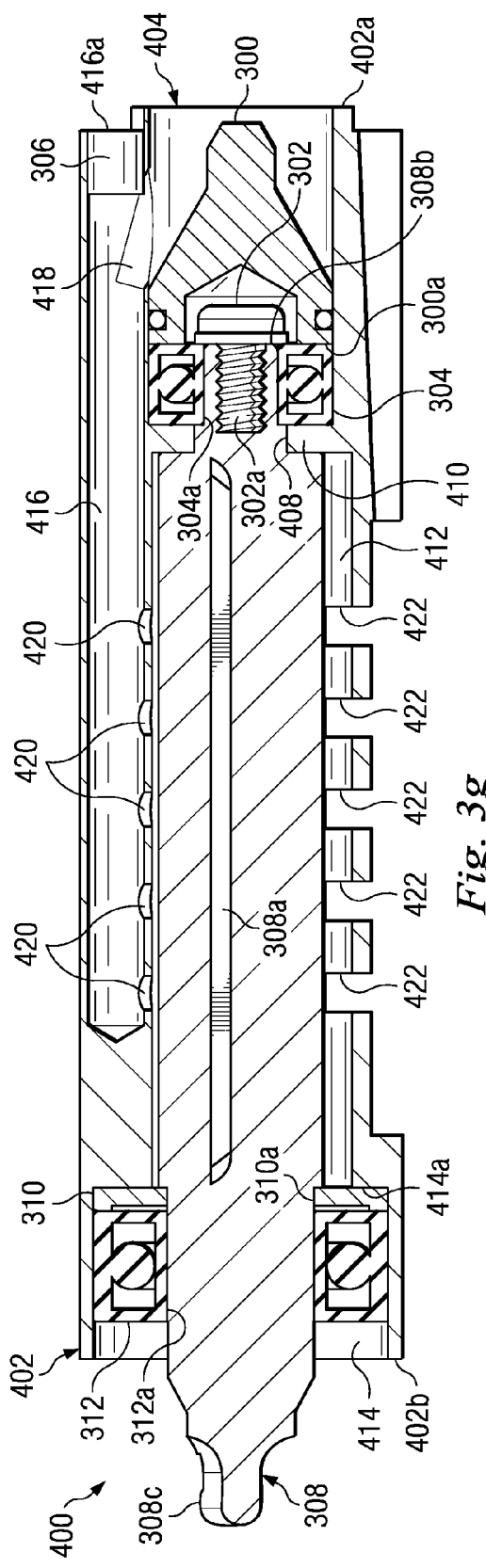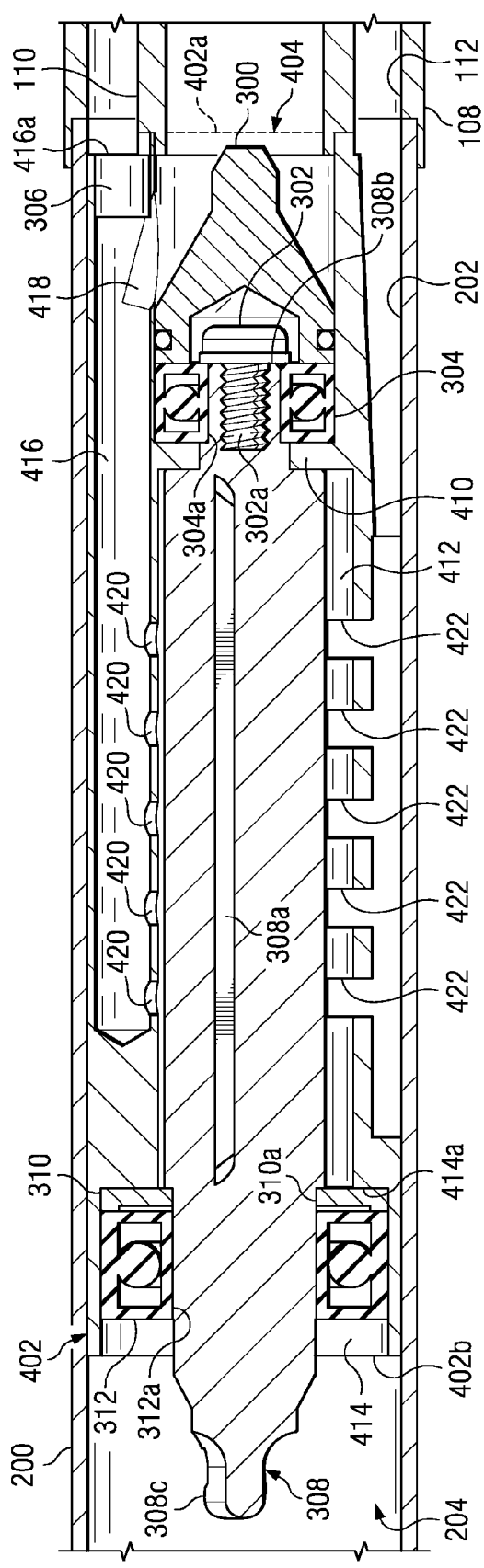

MOTOR ASSEMBLY FOR A POWERED SURGICAL INSTRUMENT

FIELD OF THE INVENTION

The present disclosure generally relates to surgical instruments and in particular to surgical instruments for dissecting bone and other tissue.

BACKGROUND

Motorized surgical instruments may use a variety of method to power moving components. For example, a motorized surgical instrument used for dissecting bone or tissue may use a pneumatic motor to power a dissecting tool. Pressurized fluid power the motor, which may be mechanically linked to the dissecting tool by means of a rotatable shaft. The application of pressurized fluid to the motor results in rotation of the shaft, which in turn rotates the dissecting tool.

Difficulties may arise in the assembly and operation of pneumatic surgical instruments. Conventional pneumatic surgical instruments house the rotatable shaft in a rotor housing chamber defined by a rotor housing. In order to allow the shaft to rotate freely in the rotor housing chamber, a plurality of components are coupled to the rotor housing such as, for example, bearings, bearing housings, fluid distributors, and a variety of other components known in the art. In addition, in order to ensure that these components are properly positioned in the assembly, an alignment pin may be used to align the components with the rotor housing and the shaft. As the number of components coupled to the rotor housing grows, the tolerance between the components and the rotor housing make the repeatability of the assembly of the surgical instrument itself difficult.

Therefore, what is needed is an improved assembly for a surgical instrument.

SUMMARY

The present disclosure provides many technological advances that can be used, either alone or in combination, to provide an improved motor assembly for a powered surgical instrument and/or an improved system and method for using powered surgical instruments.

In one embodiment, a housing member for a powered surgical instrument comprises a one-piece base, a rotor housing chamber defined by the base, a first bearing housing defined by the base and located adjacent the rotor housing chamber, a second bearing housing defined by the base and located on an opposite side of the rotor housing chamber from the first bearing housing, and a passage defined by the base and operable to direct a pressurized fluid through the base to the rotor housing chamber.

Further forms and embodiments will become apparent from the detailed description provided hereinafter. It should be understood that the detailed description and specific examples, while indicating preferred embodiments, are intended for purposes of illustration only and are not intended to be limiting.

BRIEF DESCRIPTION OF THE DRAWINGS

The present disclosure will become more fully understood from the detailed description and the accompanying drawings, wherein:

FIG. 3b is a perspective view illustrating an embodiment of a housing member used in the surgical instrument of FIG. 2 and illustrated in FIG. 3a.

FIG. 3g is a partial cross-sectional view illustrating an embodiment of a portion of the assembled surgical instrument illustrated in FIG. 3c.

FIG. 4 is a partial cross sectional view illustrating an embodiment of a portion of the surgical instrument illustrated in FIG. 2.

DETAILED DESCRIPTION

Figure 1:
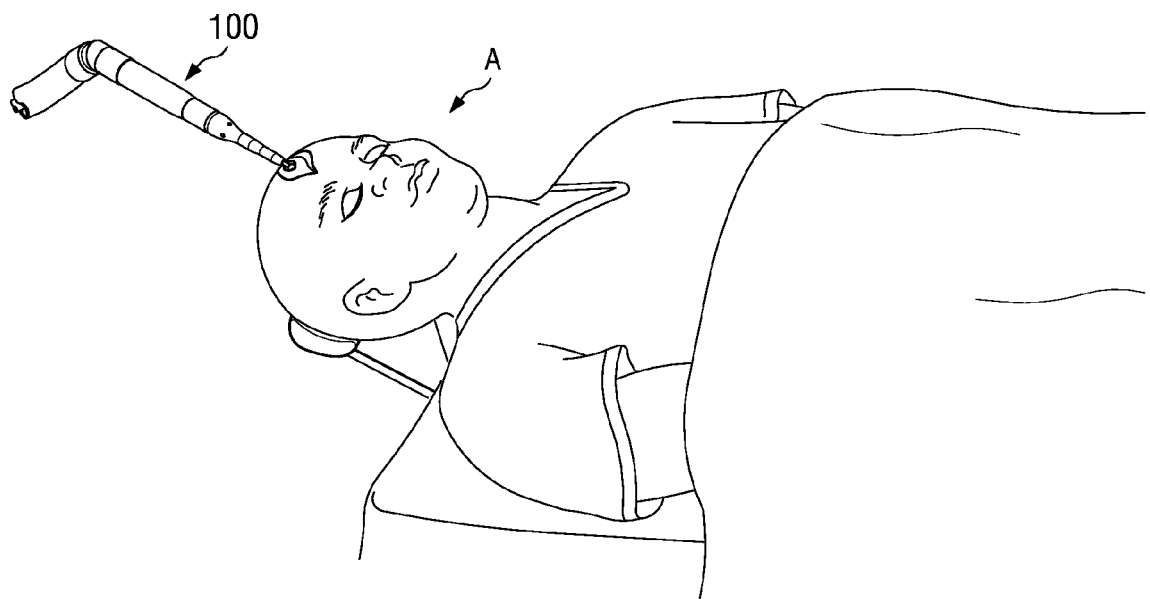
FIG. 1 is an environmental view illustrating an embodiment of a surgical instrument for the dissection of bone and other tissue according to the teachings of an embodiment of the present disclosure operatively associated with a patient for performing a craniotomy.

The present disclosure relates to surgical tools, and more particularly, to a housing member and motor assembly for use in powered surgical instruments. It is understood, however, that the following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Referring initially to FIG. 1, a surgical instrument for the dissection of bone and other tissue constructed in accordance with the teachings of a first preferred embodiment of the present invention is illustrated and generally identified at reference numeral 100. The surgical instrument 100 is shown operatively associated with a patient A for performing a craniotomy. It will become apparent to those skilled in the art that the subject invention is not limited to any particular surgical application but has utility for various applications in which it is desired to dissect bone or other tissue.

Figure 2:
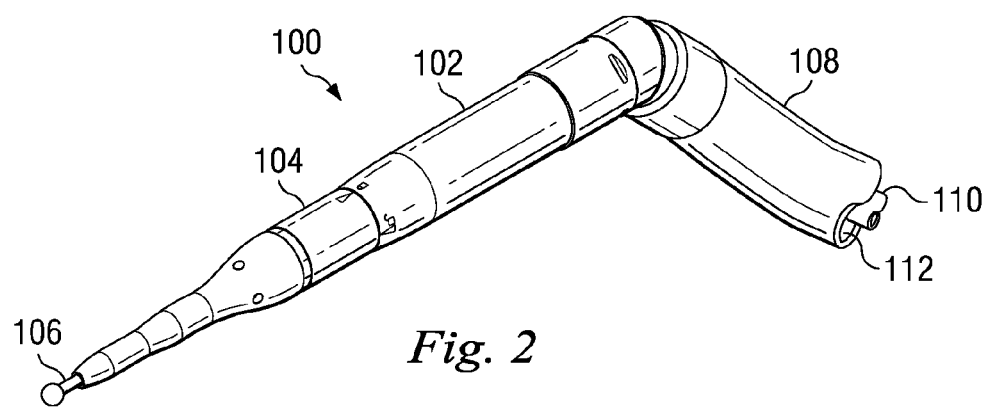
FIG. 2 is a perspective view illustrating an embodiment of the surgical instrument for the dissection of bone and other tissue according to the teachings of an embodiment of the present disclosure, the surgical instrument shown operatively associated with a hose assembly.

With reference to FIG. 2, the surgical instrument 100 is illustrated to generally include a motor assembly 102, an attachment 104 coupled to the motor assembly 102, and a surgical tool 106 coupled to the attachment 104 and the motor assembly 102. In the preferred embodiment, the surgical tool 106 is a cutting tool or dissection tool, although the type of tool is not essential to implementing the present invention. A distal end of the dissection tool 106 includes an element adapted for a particular procedure, such as a cutting element.

The attachment 104 may provide a gripping surface for use by a surgeon and may also shield underlying portions of the instrument 100 during a surgical procedure.

The surgical instrument 100 is shown connected to a hose assembly 108 for providing a source of pressurized fluid (e.g., air or nitrogen) to the motor assembly 102 through a tube 110 and a passageway 112 in the hose assembly 108 for exhausting fluid after passing through the motor assembly 102. Typically, the hose assembly 108 is connected to a filter system (not shown) spaced from the patient and the exhaust fluid is allowed to exit the system after passing through the filter system. In the exemplary embodiments that will be described, the surgical instrument 100 is pneumatically powered. It is further understood, however, that many of the teaching discussed herein will have equal application for surgical instruments using other sources of power.

Figure 3A:
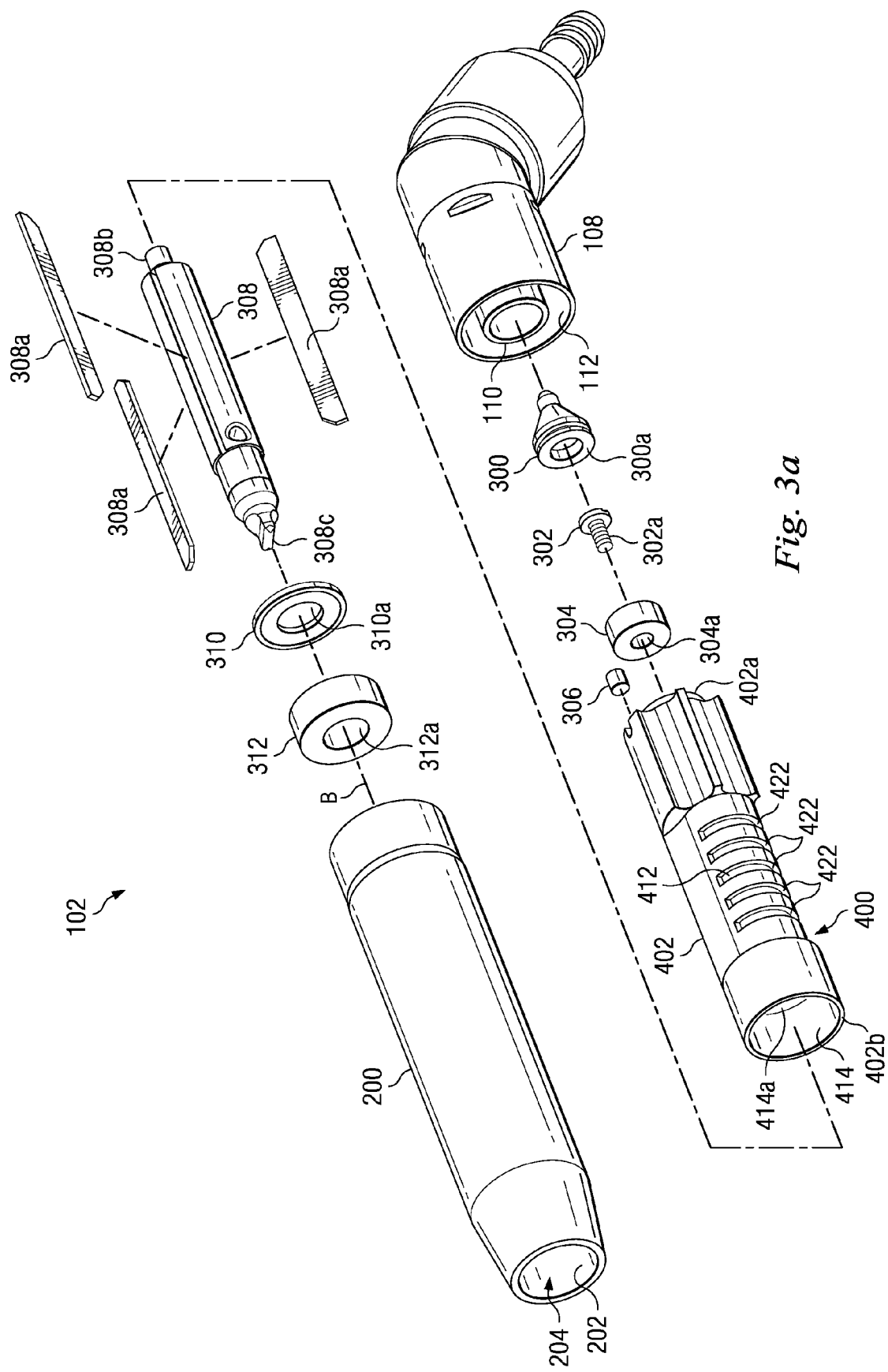
FIG. 3a is an exploded perspective view illustrating an embodiment of a portion of the surgical instrument of FIG. 2.
Figure 3B:
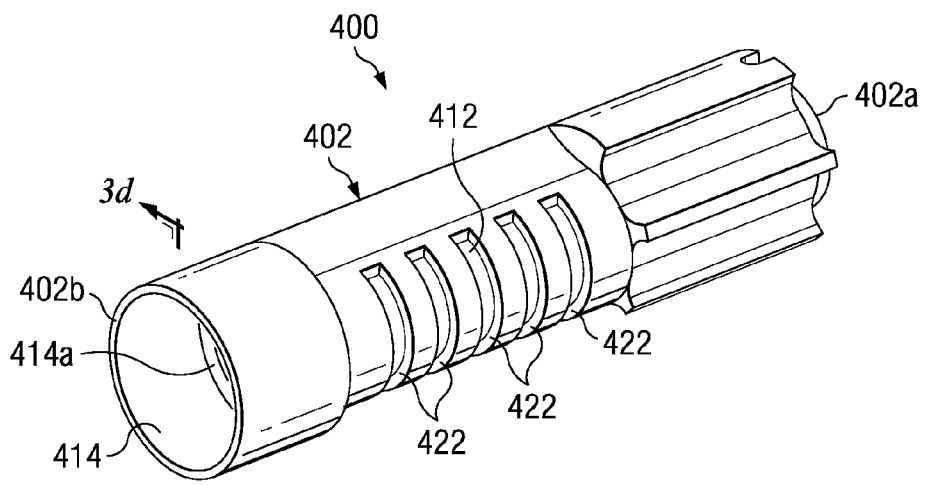
Figure 3C:
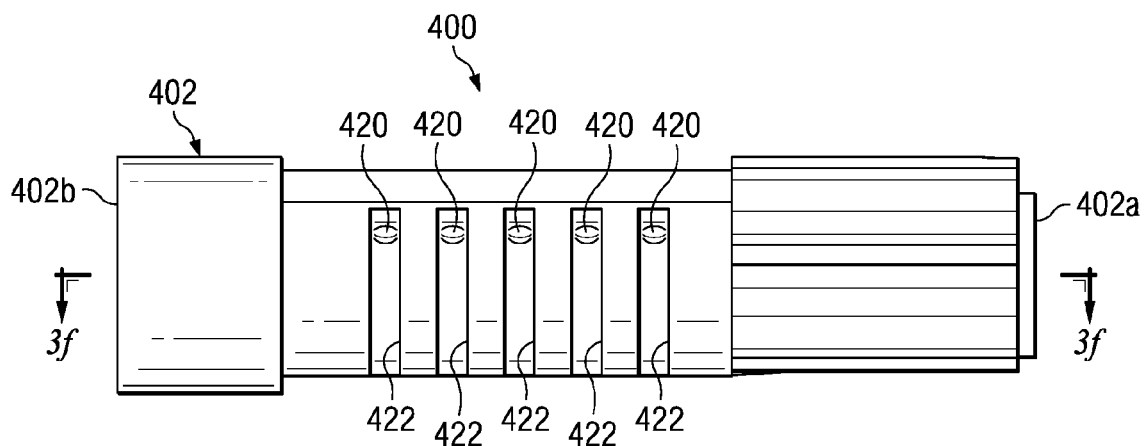
FIG. 3c is a side view illustrating an embodiment of the housing member illustrated in FIG. 3b.
Figure 3D:
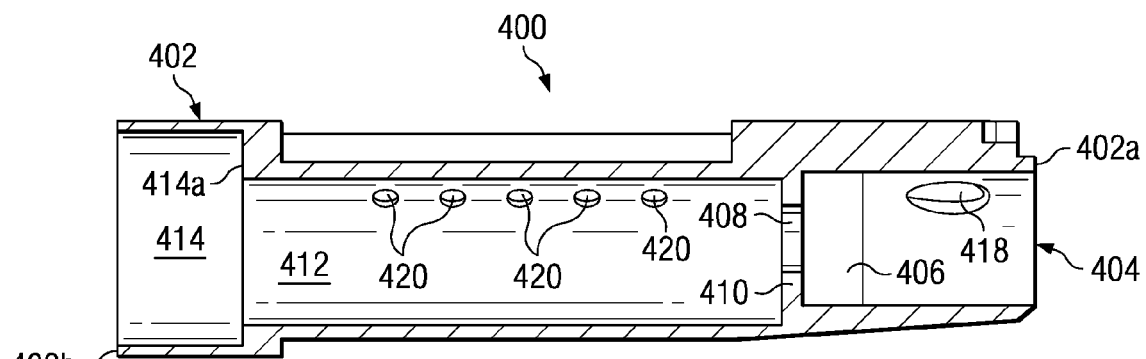
FIG. 3d is a cross sectional view illustrating an embodiment of the housing member illustrated in FIG. 3b taken along the line 3d-3d in FIG. 3b.
Figure 3E:
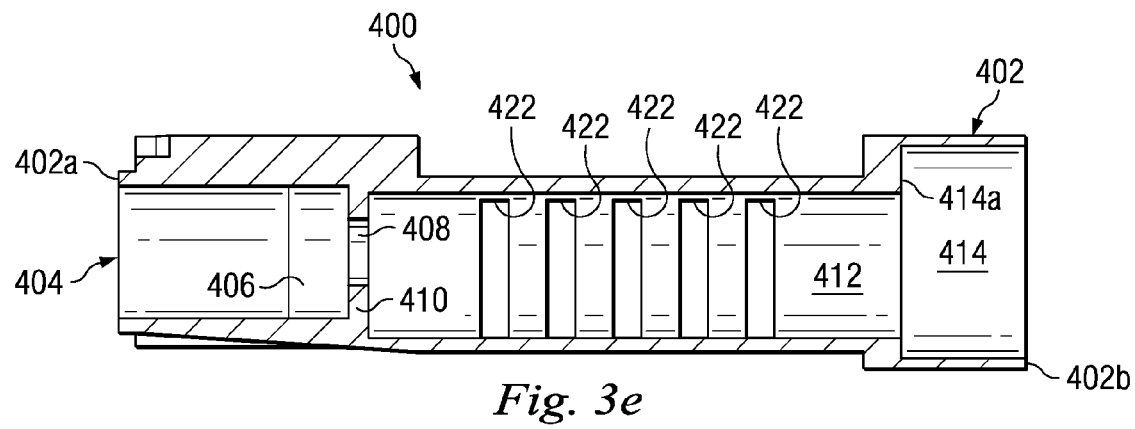
FIG. 3e is a cross sectional view illustrating an embodiment of the remaining portion of the housing member illustrated in FIG. 3b and not shown in FIG. 3d.
Figure 3F:
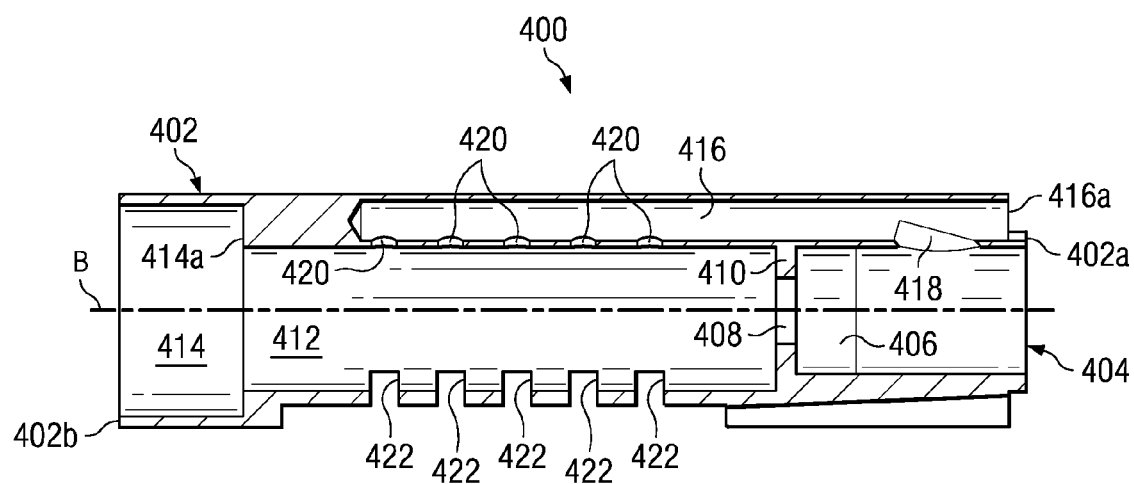
FIG. 3f is a cross sectional view illustrating an embodiment of the rotor housing illustrated in FIG. b taken along line 3f-3f in FIG. 3c.

Referring now to FIG. 3a, one embodiment of the motor assembly 102 of FIG. 2 is shown in detail. The motor assembly 102 includes a motor housing 200 having an internal surface 202 defining a generally cylindrical internal chamber 204. The motor housing 200 may include, for example, internal shoulders (not shown) extending into the internal chamber 204 and seals (not shown) for creating a seal between the motor housing 200 and the other components of the motor assembly 102, described in further detail below. The seals may be made from a material comprising a compounded form of PTFE fluorocarbons and other inert ingredients, such as the product RULON-J. This material provides the seals with a relatively low coefficient of friction while requiring little or no lubrication.

The motor assembly 102 further includes a bearing retainer member 300 having a bearing engagement surface 300a, a fastener 302 including a coupling member 302a, a first bearing 304 defining a first bearing aperture 304a, a plug 306, a rotatable shaft 308 including a plurality of vanes 308a extending along its length and a pair of opposing coupling ends 308b and 308c, a bearing plate 310 defining a bearing plate aperture 310a, and a second bearing 312 defining a second bearing aperture 312a, all located in and/or coupled to a housing member 400 in a manner described in further detail below Referring now to FIGS. 3a, 3b, 3c, 3d, 3e, and 3f, the housing member 400 includes an elongated and generally cylindrically shaped one-piece base 402 having a first end 402a and a second end 402b located opposite the first end 402a. In the illustrated embodiment, housing member 400 is a unitary piece of material with various features, described below, defined either in or into the material. Although a unitary, homogenous material is shown forming housing member 400, it is contemplated that non-homogenous material such as, for example, a substrate material coated with a different material, may be joined to form the one-piece housing member 400. In an embodiment, the housing member 400 is fabricated from stainless steel. In an embodiment, the housing member 400 may be fabricated from ceramic and/or may include a coating in order to make the housing member 400 more resistant to abrasive wear. In an embodiment, the housing member is machined. A pressurized fluid inlet 404 is defined by the base 402 and extends from the first end 402a of the base 402 along a longitudinal axis B of the base 402 towards the second end 402b of the base 402. A first bearing housing 406 is defined by the base 402 and is located immediately adjacent the pressurized fluid inlet 404. A coupling aperture 408 is defined by the base 402 by an internal flange 410 that is located immediately adjacent the first bearing housing 406. A rotor housing chamber 412 is defined by the base 402 and located immediately adjacent the internal flange 410 and the coupling aperture 408 opposite the first bearing housing 406. A second bearing housing 414 is defined by the base 402 and extends between a plate engagement wall 414a adjacent the rotor housing chamber 412 and the second end 402b of the base 402. A passage 416 is defined by the base 402 and extends in a substantially parallel orientation but radially spaced apart from the longitudinal axis B of the base 402 from a passage entrance 416a such that the passage 416 is axially co-located adjacent the pressurized fluid inlet 404, the first bearing housing 406, the internal flange 410, and a portion of the rotor housing chamber 412. A passage entrance 418 is defined by the base 402 oriented at an angle to the passage 416 and provides a fluid passageway between the pressurized fluid inlet 404 and the passage 416. In the illustrated embodiment, the passage entrance 418 is oriented at a 45 degree angle to the passage 416. A plurality of rotor housing high pressure fluid entrances 420 are defined by the base 402 and provide a fluid passageway between the high pressure passage 416 and the rotor housing chamber 412. A plurality of rotor housing fluid exists 422 are defined by the base 402 and provide a fluid passageway between the rotor housing chamber 412 and outside of the base 402.

Referring now particularly to FIGS. 3a and 3g, in an assembled form, the plurality of vanes 308a are attached to the rotatable shaft 308, which is positioned within the rotor housing chamber 412 of the base 402. The coupling end 308b of the rotatable shaft 308 extends through the coupling aperture 408 and into the first bearing housing 406, and the coupling end 308c of the rotatable shaft 308 extends through the second bearing housing 414 and out past the second end 402b of the base 402. The bearing plate 310 is located in the second bearing housing 414 and in engagement with the plate engagement wall 414a such that the rotatable shaft 308 extends through the bearing plate aperture 310a defined by the bearing plate 310. The second bearing 312 is located in the second bearing housing 414 and in engagement with the bearing plate 310 such that the rotatable shaft 308 extends through the second bearing aperture 312a and is rotatably supported by the second bearing 312. In the illustrated embodiment, the second bearing 312 is maintained in position by a frictional engagement or interference fit with the internal wall of the bearing housing 414. In an alternative embodiment, adhesives may be used to maintain the second bearing 312 in position.

The first bearing 304 is located in the first bearing housing 406 and in engagement with the internal flange 410 such that the coupling end 308b of the rotatable shaft 308 extends into the first bearing aperture 304a and is rotatably supported by the first bearing 304. The coupling member 302a on the fastener 302 engages the coupling end 308b on the rotatable shaft 308 and the fastener 302 engages the first bearing 304. The bearing retainer member 300 is located partially in the first bearing housing 406 and the pressurized fluid inlet 404 such that the bearing engagement surface 300a engages the first bearing 304. The plug 306 is located in the passage opening 416a such that pressurized fluid in the passage 416 may not escape the passage 416 through the passage opening 416a. In the illustrated embodiment, the passage opening 416a is a result of the fabrication of the passage 416, which requires the passage 416 be drilled into the base 402 from the first end 402a of the housing member 402. The plug 306 is then press fit permanently into the passage opening 416a in order to prevent pressurized fluid from escaping from the passage 461 through the passage opening 416a. However, alternative embodiments may include fabrication techniques for the passage 416 that eliminate the passage opening 416a and the need for the plug 306, such as the alternative embodiment 500 described below and illustrated in FIG. 5. In a further embodiment, additional seals may be provided in the housing member 400 such that a fluid tight passageway is provided between the first bearing housing 406, the rotor housing chamber 412, and the second bearing housing 414 and pressurized fluid introduced into the passage 416 flows through the rotor housing fluid entrances 420, into the rotor housing chamber 412, and out of the rotor housing fluid exists 422 and does not escape through the first bearing housing 406 or the second bearing housing 414.

With continued reference to FIGS. 3a and 3g, and with additional reference to FIG. 4, in operation, the housing member 400 including the bearing retainer member 300, the fastener 302, the first bearing 304, the plug 306, the rotatable shaft 308, the bearing plate 310, and the second bearing 312, is positioned in the internal chamber 204 in the motor housing 200. In the illustrated embodiment, the engagement between the housing member 400 and the motor housing 200 allows exhaust pressure to surround the housing member 400 such that a majority of the exhaust pressure flows into the hose assembly 108 and through the passageway 112. In another embodiment, the engagement between the housing member 400 and the motor housing 200 creates a fluid tight seal. In a further embodiment, fluid tight seals are provided between the housing member 400 and the motor housing 200. The hose assembly 108 is then coupled to the motor housing 200 such that the tube 110 is coupled to the first end 402a of the housing member 402 and provides a sealed passageway for pressurized fluid between the tube 110 and the pressurized fluid inlet 404. A seal is also provided between the hose assembly 108 and the motor housing 200. The coupling end 308c of the rotatable shaft 308 may be coupled to the surgical tool 106 (not shown) using, for example, a collet.

Pressurized fluid in the range of 0 to 150 PSI then enters the pressurized fluid inlet 404 from the tube 110 in the hose assembly 108, and a control may be provided to allow a user of the surgical instrument 100 to adjust the pressure of the pressurized fluid between this range. In an embodiment, the pressure of the pressurized fluid upstream of the motor assembly is set at 120 PSI. In an embodiment, the pressure of the pressurized fluid upstream of the motor assembly is set at 100 PSI. In an embodiment, pressure losses in the pressurized fluid upstream of the motor assembly may be between 10 to 30 PSI. The pressurized fluid is directed into the passage 416 through the passage entrance 418 due to the seal between the bearing retaining member 300 and the first bearing 304 and the seal between the plug 306 and the passage opening 416a. The pressurized fluid is then directed into the rotor housing chamber 412 through the rotor housing fluid entrances 420. As the pressurized fluid moves through the rotor housing chamber 412 from the rotor housing fluid entrances 420 towards rotor housing fluid exits 422, the fluid impacts the vanes 308a and causes rotation of the rotatable shaft 308. In an embodiment, the centerline of the rotatable shaft 308 may be offset from the centerline of the rotor housing chamber 412 in order to create increased torque relative to when the centerlines of the rotatable shaft 308 and the rotor housing chamber 412 are co-linear. The lower pressure fluid then exits the rotor housing chamber 412 through the rotor housing fluid exits 422 and travels back through the exhaust fluid passageway 112 in the hose assembly 108 between the tube 110 and the hose assembly 108. In an embodiment, the fluid loses pressure due to expansion and energy exchange and may be, for example, between 20-30 PSI dynamic when the pressure of the fluid upstream of the motor assembly 102 is 120 PSI. Thus, a surgical instrument is provided that includes a housing member that allows for a simplified assembly of the motor assembly relative to a convention rotor housing and decreases the passageways available to provide a fluid leak by reducing the number of components used in the motor assembly. While the surgical instrument 100 has been described as being powered pneumatically by a gas fluid, other powering schemes are contemplated such as, for example, hydraulically powering the surgical instrument with a liquid fluid.

Figure 5:
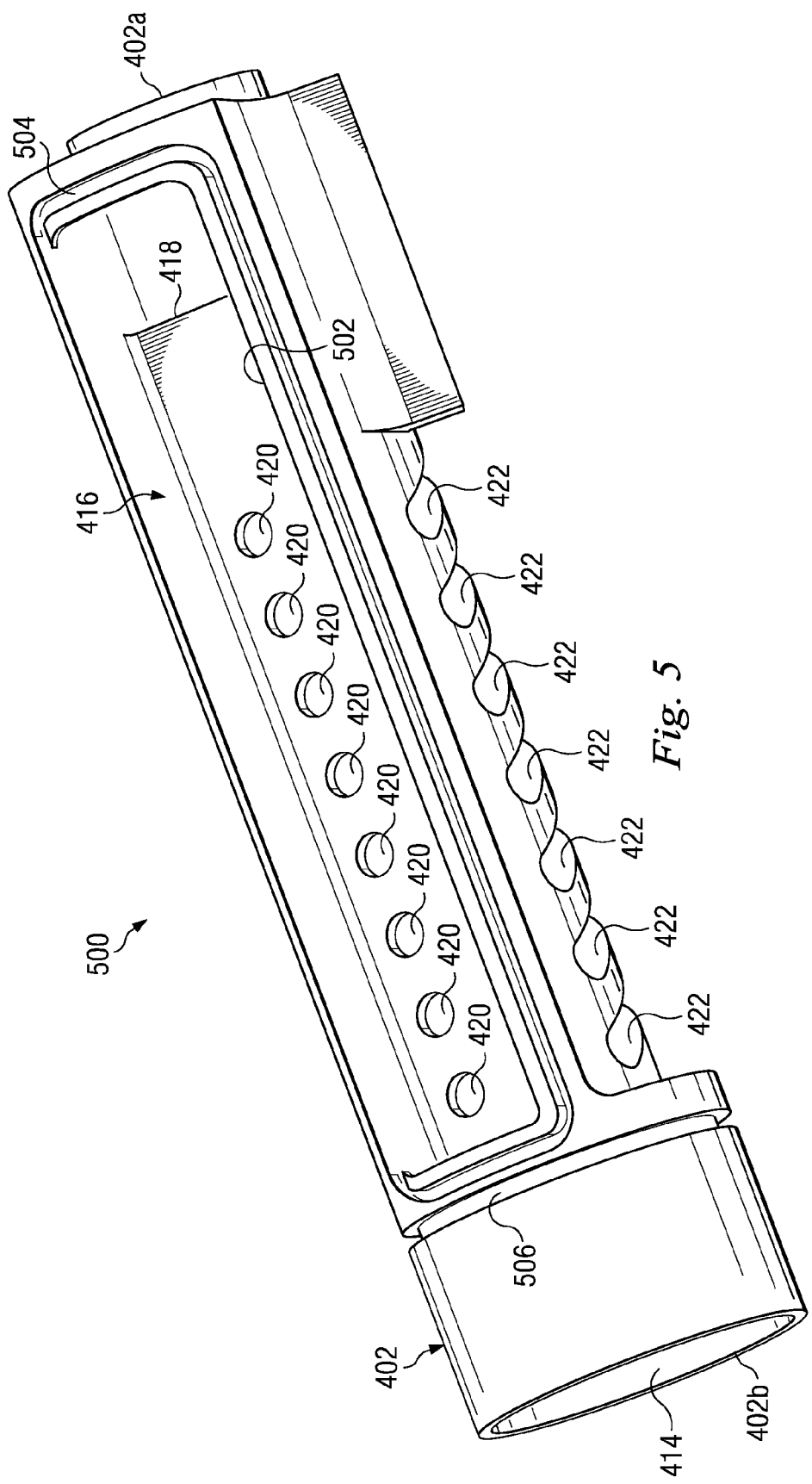
FIG. 5 is a perspective view illustrating an alternative embodiment of a housing member.

Referring now to FIG. 5, in an alternative embodiment, a housing member 500 is substantially similar in design and operation to the housing member 400, described above with reference to FIGS. 3a, 3b, 3c, 3d, 3e, 3f, 3g, and 4, with the provision of an opening 502 defined by the base 402 of the housing member 500 that is located adjacent the passage 416. A seal groove 504 is defined by the base 402 and is located about the perimeter of the opening 502. A seal groove 506 is defined by the base 402 and is located about the circumference of the base 402 and between the opening 502 and the second end 402b of the base 402. In assembly, the housing member 500 is positioned in the internal chamber 204 of the motor housing 200 in substantially the same manner as described above for the housing member 400, with the provision of seals (not shown) located in the seal grooves 504 and 506 such that the seals engage the internal surface 202 of the motor housing 200 and provide a fluid tight seal between the housing member 500 and the motor housing 200. In operation, the housing member 500 operates substantially similarly to the housing member 400, with the seals in the seal grooves 504 and 506 directing pressurized fluid through the passage 416 and into the rotor housing high pressure fluid entrances 420. Provision of the opening 502 provides a larger volume for the pressurized fluid to travel through the housing member 500 relative to the housing member 400 and reduces the pressure drop experienced by the pressurized fluid when it travels through the passage 416 of the housing member 500 relative to the housing member 400. Furthermore, the opening 502 allows fabrication of the passage 416 without the need to fabricate the passage opening 416a and eliminates the need for the plug 306.

While the invention has been particularly shown and described with reference to the preferred embodiment thereof, it will be understood by those skilled in the art that various changes in form and detail many be made therein without departing from the spirit and scope of the invention. Furthermore, the housings and/or components may be replaced by other suitable elements to achieve similar results. In addition, a variety of materials may be used to form the various components and the relative sizes of components may be varied. Therefore, the claims should be interpreted in a broad manner, consistent with the present invention.

What is claimed is:

1. An assembly for a motorized surgical instrument, the assembly comprising:
   a one-piece base having an external base wall extending along a first longitudinal axis between a first base end and a second base end and having:
   at least one transverse wall extending transverse to the first longitudinal axis and towards an interior of the one-piece base,
   a rotor housing chamber defined by the base within the external base wall and between at least a first transverse wall of the at least one transverse wall and the second base end,
   a first bearing housing defined by the base between the first base end and the first transverse wall located adjacent the rotor housing chamber, a second bearing housing defined by the base between the second base end and a plate wall located on an opposite side of the rotor housing chamber from the first bearing housing,
a bearing located in the second bearing housing configured to engage a rotatable shaft, and
a passage defined by the base and extending along a second longitudinal axis offset from the first longitudinal axis and along an exterior of the first bearing housing and the rotor housing chamber, the passage configured to direct a pressurized fluid through the base to the rotor housing chamber;
wherein the rotor housing chamber, the first bearing housing, the second bearing housing, and the at least one transverse wall are one-piece with the one-piece base.

2. The assembly of claim 1, further comprising:
a pressurized fluid inlet defined by the base and located on an opposite side of the first bearing housing from the rotor housing chamber.

3. The assembly of claim 2, further comprising:
a passage entrance defined by the base and located between the first bearing housing and the pressurized fluid inlet, whereby pressurized fluid entering the pressurized fluid inlet enters the passage through the passage entrance.

4. The assembly of claim 1, further comprising:
a rotor housing fluid entrance defined by the base, whereby pressurized fluid in the passage enters the rotor housing chamber through the rotor housing fluid entrance; and
a rotor housing fluid exit defined by the base, whereby fluid in the rotor housing chamber exits the rotor housing chamber through the rotor housing fluid exit.

5. The assembly of claim 1, further comprising:
a passage opening defined by the base and operable to accept a plug.

6. The assembly of claim 1, further comprising:
a motor housing having a motor housing wall defining an internal bore;
wherein the one-piece base is formed as a unitary piece and is configured to be positioned within the internal bore of the motor housing.

7. The assembly of claim 6, further comprising:
a hose assembly having a tube inlet and an exhaust outlet;
wherein the tube inlet is configured to connect to the motor housing and direct a pressurized fluid to the passage.

8. An assembly for a motorized surgical instrument, the assembly comprising:
a one-piece base extending along a first longitudinal axis between a first base end and a second base end, the one-piece base comprising:
at least one transversely extending wall extending substantially perpendicular to the first longitudinal axis towards an interior of the one-piece base,
a rotor housing chamber defined by the base,
a first bearing housing defined by the base and located adjacent the rotor housing chamber between the first base end and the at least one of the at least one transversely extending wall,
a second bearing housing defined by the base and located on an opposite side of the rotor housing chamber from the first bearing housing, and
a passage defined by the base and operable to direct a pressurized fluid through the base to the rotor housing chamber;
a first bearing located in the first bearing housing;
a rotatable shaft located in the rotor housing chamber and engaging the first bearing; and
a second bearing located in the second bearing housing, wherein the rotatable shaft engages the second bearing.

9. The assembly of claim 8,
wherein the one-piece base further comprises a bearing plate located in the second bearing housing and adjacent the second bearing.

10. The assembly of claim 8, further comprising:
a fastener located at least partially in the first bearing housing and engaging the first bearing and the rotatable shaft.

11. The assembly of claim 8, further comprising:
a bearing retainer member located at least partially in the first bearing housing and engaging the first bearing.

12. The assembly of claim 8,
wherein the one-piece base further comprises a pressurized fluid inlet defined by the base and located on an opposite side of the first bearing housing and first bearing from the rotor housing chamber.

13. The assembly of claim 12,
wherein the one-piece base further comprises a passage entrance defined by the base and located between the first bearing housing and the pressurized fluid inlet, whereby pressurized fluid entering the pressurized fluid inlet enters the passage through the passage entrance.

14. The assembly of claim 13,
wherein the one-piece base further comprises a rotor housing fluid entrance defined by the base, whereby pressurized fluid in the passage enters the rotor housing chamber through the rotor housing fluid entrance and engages the rotatable shaft; and
wherein the one-piece base further comprises a rotor housing fluid exit defined by the base, whereby fluid in the rotor housing chamber exits the rotor housing chamber through the rotor housing fluid exit.

15. The assembly of claim 14,
wherein the one-piece base further comprises a passage opening defined by the base and operable to accept a plug.

16. The assembly of claim 14, further comprising:
a motor housing having a motor housing wall defining an internal bore;
wherein the one-piece base is formed as a unitary piece and is configured to be positioned within the internal bore of the motor housing.

17. A method for a powered surgical instrument, the method comprising:
providing a unitarily formed one-piece base extending along a first longitudinal axis from a first base end to a second base end having:
at least one transverse wall extending substantially perpendicular to the first longitudinal axis,
a rotor housing chamber,
a first bearing housing adjacent the rotor housing chamber,
a passage coupled to the rotor housing chamber,
a second bearing housing located opposite the rotor housing chamber from the first bearing housing; and
providing a second bearing located in the second bearing housing that engages the rotatable shaft;
providing a first bearing located in the first bearing housing; and
providing a rotatable shaft located in the rotor housing chamber and engaging the first bearing located in the first bearing housing;
wherein the rotor housing chamber and the first bearing housing are separated by the at least one transverse wall of the one-piece base.

18. The method of claim 17, further comprising:
providing a substantially fluid tight seal between the rotor housing chamber and the first bearing housing, and providing a substantially fluid tight seal between the rotor housing chamber and the second bearing housing.

19. The method of claim 18, further comprising:
forming a pressurized fluid inlet in the one-piece base that is oriented at an angle to the passage.

20. The method of claim 17, further comprising:
providing a plug to seal an opening in the passage separate from a pressurized fluid inlet;
wherein the passage is formed by drilling into the base from near the first base end generally parallel to the first longitudinal axis.

* * * * *